United States Patent [19]

Steiner et al.

[11] Patent Number: 4,469,896
[45] Date of Patent: Sep. 4, 1984

[54] PROCESS FOR THE PRODUCTION OF CHLOROPYRIDINES SUBSTITUTED BY METHYL, TRICHLOROMETHYL OR TRIFLUOROMETHYL GROUPS

[75] Inventors: Eginhard Steiner, Füllinsdorf; Pierre Martin, Rheinfelden, both of Switzerland

[73] Assignee: Ciba-Geigy Corporation, Ardsley, N.Y.

[21] Appl. No.: 512,085

[22] Filed: Jul. 8, 1983

Related U.S. Application Data

[62] Division of Ser. No. 293,804, Aug. 17, 1981, abandoned.

[51] Int. Cl.$^3$ ............................................. C07C 47/14
[52] U.S. Cl. ..................................... 568/495; 568/448
[58] Field of Search ........................ 568/469, 495, 448

[56] References Cited

U.S. PATENT DOCUMENTS 2,568,500  9/1951  Housted et al. ..................... 568/495

OTHER PUBLICATIONS

Bekker et al., "Chemical Abstracts", vol. 83, (1975), p. 147,047t.

*Primary Examiner*—Werren B. Lone

*Attorney, Agent, or Firm*—Karl F. Jorda

[57] ABSTRACT

Chloropyridines of the formula

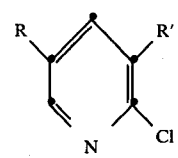

wherein either R is chlorine and R' is methyl or trifluoromethyl, or R is methyl, trichloromethyl or trifluoromethyl and R' is chlorine, or R and R' are methyl, can be obtained by a novel, simple process by the addition of trichloroacetaldehyde to methacrylonitrile or α-trifluoromethacrylonitrile, 2,2-dichloropropionaldehyde, pentachloropropionaldehyde or 2,2-dichloro-3,3,3-trifluoropropionaldehyde to acrylonitrile, or 2,2-dichloropropionaldehyde to methacrylonitrile, in the presence of a catalyst, in particular copper powder or copper(I) chloride, and cyclizing the open-chain intermediate obtained.

The chloropyridines of the formula (I) are known per se and are suitable for the production of different compounds, in particular of insecticides and herbicides.

1 Claim, No Drawings

PROCESS FOR THE PRODUCTION OF CHLOROPYRIDINES SUBSTITUTED BY METHYL, TRICHLOROMETHYL OR TRIFLUOROMETHYL GROUPS

This is a divisional of application Ser. No. 293,804 filed on Aug. 17, 1981, now abandoned.

The present invention relates to a novel process for the production of chloropyridines substituted by methyl, trichloromethyl or trifluoromethyl groups, and to the novel intermediates obtained in said process.

Up to now it was possible to obtain chloropyridines substituted by methyl, trichloromethyl or trifluoromethyl groups only by means of complicated multi-step processes. For example, 2,5-dichloro-3-methylpyridine and 2,3-dichloro-5-methylpyridine can be obtained by diazotising 2-chloro-3-methyl-5-aminopyridine and 2-chloro-3-amino-5-methylpyridine respectively and replacing the diazo group with chlorine.

The above aminopyridines can be obtained by chlorinating 3-methylpyridine to 2-chloro-3-methylpyridine and 2-chloro-5-methylpyridine, nitrating these latter compounds to 2-chloro-3-methyl-5-nitropyridine and 2-chloro-3-nitromethylpyridine and reducing the nitro compounds. When chlorinating 3-methylpyridine, several isomers are usually obtained in addition to the desired compound. Chlorination of 2,3-dichloro-5-methylpyridine gives 2,3-dichloro-5-trichloromethylpyridine, which can be converted into 2,3-dichloro-5-trifluoromethylpyridine by replacing the chlorine atoms of the trichloromethyl group by fluorine atoms (q.v. for example European patent publication 004414). In addition to 5 other isomers, 2-chloro-3,5-dimethylpyridine is obtained by heating 2,4-dimethylpyrrole and chloroform in the gas phase at temperatures of about 550° C. [q.v. J. Chem. Soc. Perkin Trans. I, 1578–82 (1979)].

It has now been found that chloropyridines of the formula I,

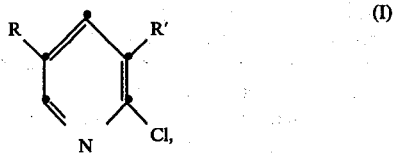

wherein either R is chlorine and R' is methyl or trifluoromethyl, or R is methyl, trichloromethyl or trifluoromethyl and R' is chlorine, or R and R' are methyl, can be obtained in very simple, economical and environmentally safe manner, in good yield and using readily obtainable cheap starting materials, by the addition of
(a) trichloroacetaldehyde to methacrylonitrile or α-trifluoromethacrylonitrile,
(b) 2,2-dichloropropionaldehyde, pentachloropropionaldehyde or 2,2-dichloro-3,3,3-trifluoropropionaldehyde to acrylonitrile, or
(c) 2,2-dichloropropionaldehyde to methacrylonitrile, in the presence of a catalyst, and cyclising the intermediate of the formula II

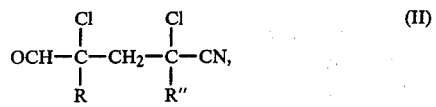

wherein either R is chlorine and R" is methyl or trifluoromethyl, or R is methyl, trichloromethyl or trifluoromethyl and R" is hydrogen, or R and R" are methyl, to give a compound of the formula I.

A formally identical reaction scheme of non-alkyl-substituted trichloroformylbutyronitrile to give 2,3,5-trichloropyridine is described in European patent publication No. 12117. However, the cyclisation with aromatisation to give chlorinated methyl- and trihalomethylpyridines of the formula I from chlorinated and methyl- or trihalomethyl-substituted formylbutyronitriles of the formula II was not to be expected, as the elimination of water necessary for the aromatisation to form the methyl or trihalomethyl radical at the ring is no longer possible in the process of this invention. The expected outcome would therefore more likely have been the formation of a 2-pyridone derivative. The reaction sequence of this invention must therefore be termed most surprising. The formation of the addition compounds of the formula II from 2,2-dichloropropionaldehyde, perchloro- or 2,2-dichloro-3,3,3-trifluoropropionaldehyde is likewise surprising, as the reactive properties of trichloroacetaldehyde are very different from those of its homologues [q.v. for example Chem. Ber., 97, 3322 (1964)] and, in particular, chlorine mobility at the chloroacetaldehyde is noticeably restricted by an additional carbon substituent such as methyl, trichloromethyl or trifluoromethyl.

The addition reactions can be carried out in an open or closed system, preferably in the temperature range from 70° to 160° C. It is preferred to carry out the addition reaction in a closed system under a pressure corresponding to the reaction temperature, e.g. in the range from 1 to 30 bars.

In the practice of this invention, suitable catalysts which can be employed for the addition reactions are metals of the main group VIII and of the subgroups VIa, VIIa, Ib and IIb of the periodic system, for example: iron, cobalt, nickel, ruthenium, palladium, chromium, molybdenum, manganese, copper, and zinc. These metals can be used either in elementary form or in the form of compounds. Examples of suitable compounds are oxides and salts, such as halides, sulfates, sulfites, sulfides, nitrates, acetates, stearates, citrates, carbonates, cyanides and rhodanides, as well as complexes with ligands, such as phosphines, phosphites, benzoyl- and acetylacetonates, nitriles, isonitriles and carbon monoxide. Representative examples are: copper(II) oxide, iron (III) oxide; copper(I), copper(II), iron(II) and iron(III) bromide, iodide and, in particular, chloride; zinc chloride, as well as the chorides of ruthenium, rhodium, palladium, cobalt and nickel; copper(II) sulfate, iron(II) and iron(III) sulfate; copper(II) nitrate and iron(III) nitrate; manganese(III) acetate, copper(II) acetate, copper(II) stearate, iron(III) citrate, copper (I) cyanide; ruthenium(II) dichloro-tris-triphenylphosphine, rhodiumdichloro-tris-triphenylphosphine; chromium and nickel acetylacetonate, copper(II) acetylacetonate, iron(III) acetylacetonate, cobalt(II) and cobalt(III) acetylacetonate, manganese(II) acetonylacetonate, copper(II) benzoylacetonate; iron carbonyl-cyclopentadienyl complex; molybdenum carbonylcyclopentadienyl complex; chromium tricarbonylaryl complexes, ruthenium(II) acetate complex, chromium and molybdenum hexacarbonyl, nickel tetracarbonyl, iron pentacarbonyl, cobalt and manganese carbonyl.

It is also possible to use mixtures of the above metals with metal compounds and/or other additives, such as copper powder, in combination with one of the aforementioned copper compounds; mixtures of copper powder with a lithium halide such as lithium chloride, or with an isocyanide such as tert-butyl isocyanide; mixtures of iron powder with iron(III) chloride, optionally with the addition of carbon monoxide; mixtures of iron(III) chloride with benzoin; mixtures of iron(II) or iron(III) chloride with trialkylphosphites; and mixtures of iron pentacarbonyl and iodine.

Preferred catalysts are iron(II) and iron(III) salts and complexes, in particular iron(II) and iron(III) chloride, as well as iron powder; ruthenium(III) chloride, ruthenium(II) dichloro-tris-triphenylphosphine, copper powder, copper bronze, copper(I) and copper(II) salts and complexes such as copper(I) chloride, copper(II) chloride, copper(I) bromide, copper(II) bromide; copper(II) acetate, copper(II) acetylacetonate, copper(II) benzoylacetonate, copper(II) sulfate, copper(II) nitrate, copper(I) cyanide and copper(I) iodide.

Most preferred catalysts are copper powder, copper bronze, copper(I) and copper(II) chloride or bromide and copper(I) iodide, as well as mixtures thereof.

The catalysts are generally used in amounts of about 0.01 to 10 mol.%, preferably 0.1 to 5 mol. %, based on the aldehyde.

The addition of the aldehydes to the acrylonitrile, methacrylonitrile or α-trifluoromethylacrylonitrile is conveniently carried out in the presence of an inert organic solvent. Suitable solvents are those in which the catalysts are sufficiently soluble, or which are able to form complexes with the catalysts, but which are inert to the reactants. Representative examples of suitable solvents are: alkanecarbonitriles, in particular those containing 2 to 5 carbon atoms, such as acetonitrile, propionitrile and butyronitrile; 3-alkoxypropionitriles containing 1 to 2 carbon atoms in the alkoxy moiety, such as 3-methoxypropionitrile and 3-ethoxypropionitrile; aromatic nitriles, especially benzonitrile; aliphatic ketones preferably containing a total of 3 to 8 carbon atoms, such as acetone, diethyl ketone, methyl isopropyl ketone, diisopropyl ketone, and methyl tertbutyl ketone; alkyl and alkoxyalkyl esters of aliphatic monocarboxylic acids containing a total of 2 to 6 carbon atoms, such as methyl formate and ethyl formate, methyl acetate, ethyl acetate, n-butyl acetate and isobutyl acetate, as well as 1-acetoxy-2-methoxyethane; cyclic ethers such as tetrahydrofurane, tetrahydropyrane and dioxane; dialkyl ethers containing 1 to 4 carbon atoms in each of the alkyl moieties, such as diethyl ether, di-n-propyl ether and diisopropyl ether; N,N-dialkylamides of alkanecarboxylic acids containing 1 to 3 carbon atoms in the alkyl moiety such as N,N-dimethylformamide, N,N-dimethylacetamide, N,N-diethylacetamide and N,N-dimethylmethoxyacetamide; ethylene glycol and diethylene glycol dialkyl ethers containing 1 to 4 carbon atoms in each of the alkyl moieties, such as ethylene glycol dimethyl, diethyl and di-n-butyl ether; diethylene glycol diethyl and di-n-butyl ethers; and phosphoric acid tris-N,N-dimethylamide (hexametapol). Excess acrylonitrile, methacrylonitrile or α-trifluoromethacrylonitrile can also be used as solvent.

Preferred solvents for the addition ractions are alkanecarbonitriles containing 2 to 5 carbon atoms and 3-alkoxypropionitriles containing 1 to 2 carbon atoms in the alkoxy moiety, in particular acetonitrile, butyronitrile, acrylonitrile and 3-methoxypropionitrile, or the unsaturated nitriles used as reactants.

The intermediates of the formula II are novel and have been specially developed for the synthesis of the compounds of formula I. Accordingly, they likewise constitute an object of the invention. Preferred compounds of the formula II are those in which either R is chlorine and R" is methyl, or R is methyl, trichloromethyl or trifluoromethyl, and R" is hydrogen.

The cyclisation of the compounds of the formula II can be carried out in an open or closed system in the temperature range from about 0° to 220° C., preferably from about 80° to 200° C. It is preferred to carry out the cyclisation in an open system. Where the cyclisation is carried out in an open system, it is advantageous to conduct this reaction in the presence of hydrogen chloride, or in the presence of a substance which forms hydrogen chloride under the reaction conditions, such as phosgene, boron trichloride, aluminium chloride, a trialkylammonium chloride containing 1–4 carbon atoms in each of the alkyl moieties, phosphorous pentachloride, phosphoryl chloride or phosphorus trichloride. It is preferred to carry out the cyclisation in the presence of hydrogen chloride.

It is preferred to carry out the cyclisation without the addition of a solvent, in the liquid phase or in the gas phase, by merely heating the compounds of the formula II. However the cyclisation can also be carried out in the presence of an organic solvent. Examples of suitable organic solvents are: chlorinated aliphatic hydrocarbons such as chloroform, methylene chloride and tetrachlorethane; unsubstituted or chlorinated aromatic hydrocarbons such as benzene, toluene, xylenes and chlorobenzenes; N,N-dialkylamides of alkanecarboxylic acids containing 1 to 3 carbon atoms, such as N,N-dimethylformamide, N,N-dimethylacetamide, N,N-diethylacetamide and N,N-dimethylmethoxyacetamide; cyclic amides, such as N-methyl-2-pyrrolidone, N-acetyl-2-pyrrolidone and N-methyl-γ-caprolactam; amides of carbonic acid, such as tetramethylurea and dimorpholinocarbonyl; amides of phosphorous acid, of phosphoric acid, of phenylphosphonic acid or of alkylphosphonic acids containing 1 to 3 carbon atoms in the alkyl moiety, such as phosphoric triamide, phosphoric acid tris-(N,N-dimethylamide), phosphoric acid trimorpholide, phosphoric acid tripyrrolinide, phosphorous acid tris-(N,N-dimethylamide), methanephosphonic acid bis-(N,N-dimethylamide); amides of sulfuric acid or of aliphatic or aromatic sulfonic acids, such as tetramethylsulfamide, methanesulfonic acid dimethylamide, or p-toluenesulfonamide; aliphatic ketones, cyclic ethers, dialkyl ethers as well as ethylene glycol and diethylene glycol dialkyl ethers of the aforementioned type; and also phosphorus trichloride and phosphoryl chloride. Preferred solvents for the cyclisation reaction are chloroform, methylene chloride, cyclic ethers and dialkyl ether containing 1 to 4 carbon atoms in each of the alkyl moieties, particularly dioxane and diethyl ether, as well as N,N-dialkylamides of lower aliphatic carboxylic acids, preferably N,N-dimethylformamide.

The process of this invention can conveniently be carried out by first isolating the compounds of the formula II formed by the addition reaction and subsequently effecting cyclisation in a second step. The individual steps of this process are carried out as described above.

An advantageous embodiment of the process of the invention comprises reacting the aldehydes with acrylonitrile, methacrylonitrile or α-trifluoromethylacrylonitrile, in the temperature range from 70° to 160° C., in acetonitrile, butyronitrile or 3-methoxypropionitrile as solvent, in the presence of 0.1 to 5 mol.% of copper powder, copper bronze, copper(I) or copper(II) chloride or bromide or copper(I) iodide, or in the presence of a mixture of these substances, in a closed system, and then cyclising the compounds of the formula II obtained after separation of the solvent, in the temperature range from 80° to 200° C., in a closed system, in the presence of hydrogen chloride or of a substance which forms hydrogen chloride under the reaction conditions, to give the compounds of the formula I.

It is however possible to dispense with the isolation of the intermediates of the formula II, and to carry out the addition and cyclisation reactions in one operation. In this case, the reaction of the aldehydes with acrylonitrile, methacrylonitrile or α-trifluoromethylacrylonitrile to give the chloropyridines of formula I is carried out in the temperature range from about 70° to 220° C., preferably from about 130° to 200° C. This reaction can be performed either in an open system or in a closed system. If an open system is employed, it can be advantageous to perform the reaction in the presence of hydrogen chloride, or in the presence of a substance which forms hydrogen chloride under the reaction conditions. Substances of this type are for example phosgene, boron trichloride, aluminium chloride, trialkylammonium chlorides containing 1 to 4 carbon atoms in the alkyl moieties, phosphorus pentachloride, phosphoryl chloride or phosphorus trichloride. The single-step production of chloropyridines of the formula I is carried out preferably in a closed system under a pressure corresponding to the respective reaction temperature. Depending on the reaction temperature, this pressure can be e.g. in the range of 1–50 bars. The single-step synthesis of compounds of the formula I in a closed system at a pressure of 1–30 bars is particularly preferred.

This single-step synthesis is likewise carried out in the presence of a catalyst and conveniently in the presence of an inert organic solvent. Suitable catalysts and solvents are those of the kind described hereinbefore, and the particulars regarding preferred catalysts and amounts thereof previously stated, apply here also.

Preferred solvents for carrying out the single-step process are alkanecarbonitriles containing 2 to 5 carbon atoms and 3-alkoxypropionitriles containing 1 to 2 carbon atoms in the alkyl moiety. Particularly suitable solvents are acetonitrile, butyronitrile and 3-methoxypropionitrile, or an excess of the unsaturated nitriles used as reactants. When the reaction is complete, the chloropyridines can be isolated in conventional manner, for example by evaporating off the solvent and purifying the crude product by distillation or steam distillation.

A further advantageous embodiment of the process of the invention comprises reacting the aldehydes and the acrylonitrile, methacrylonitrile or α-trifluoromethylacrylonitrile in acetonitrile, butyronitrile or 3-methoxypropionitrile as solvent, in the presence of 0.1–5 mol.% of copper powder, copper bronze, copper(I) and copper(II) chloride or bromide or copper(I) iodide, or of a mixture of these substances, at 130°–200° C., in a closed system under a pressure corresponding to the respective reaction temperature applied, direct to the chloropyridines of the formula I.

The starting 2,2-dichloro-3,3,3-trifluoropropionaldehyde is also novel and has been specially developed for the synthesis of 4-formyl-2,4-dichloro-5,5,5-trifluorovaleronitrile and 2,3-dichloro-5-trifluoromethylpyridine, and accordingly constitutes a further object of the invention.

2,2-Dichloro-3,3,3-trifluoropropionaldehyde can be obtained by treating corresponding olefins with ozone and working up the reaction mass by reduction. Suitable solvents which can be employed are: organic acids such as formic acid, acetic acid, propionic acid; the esters of these acids, such as ethyl acetate, methyl acetate, ethyl formate, methyl formate; aliphatic hydrocarbons such as pentane, hexane, heptane, octane, cyclopentane, cyclohexane; chlorinated hydrocarbons such as methylene chloride, chloroform, carbon tetrachloride; or also water. Depending on the nature of the solvent employed, the reaction temperatures are in the range from −90° to +70° C., preferably from −70° to +30° C.

The reduction of the products of the ozonolysis can be effected either by direct catalytic hydrogenation with hydrogen and a noble metal catalyst such as platinum, palladium, or rhodium, which catalyst may, if desired, be applied to a carrier, or by addition of reducing agents such as zinc or dimethyl sulfide.

A preferred embodiment of this ozonolysis comprises ozonising 4,4-dichloro-5,5,5-trifluoro-2-methyl-2-pentenecarboxylic acid methyl ester in acetic acid at 20° C., then adding an aqueous suspension of zinc powder to the reaction mixture, and distilling off 2,2-dichloro-3,3,3-trifluoropropionaldehyde direct from the mixture.

The chloropyridines of the formula I can be used in a manner known per se via one or more intermediate steps for the production of different compounds, especially insecticides and herbicides (cf. for example Swiss Pat. No. 622 170, European patent publication Nos. 00176 and 04414; European patent application No. 81810181; German Offenlegungsschrift specification Nos. 2 812 649 and 2 748 636; South African Pat. No. 7 802 440; Japanese patent publication Nos. 5 4115-380, 5 5038-356, 5 5079-369 and 56-39069; and Belgian Pat. No. 862 325).

The process of the present invention is illustrated in more detail by the following Examples.

EXAMPLE 1

(a) Preparation of 4-formyl-2-methyl-2,4,4-trichlorobutyronitrile 14.7 g of trichloroacetaldehyde, 13.5 g of methacrylonitrile, 0.3 g of copper powder (activated by the method described for copper bronze in Org. Synth. Coll., Vol. III, 339) and 30 ml of acetonitrile are heated in an enamel autoclave for 15 hours to 100° C. After the mixture has cooled, the solvent is distilled off at about 40°–50° C. in a water jet vacuum. The residue is taken up in 50 ml of diethyl ether and the precipitated copper sludge is removed by filtration. The diethyl ether is distilled off and the residue is rectified in a high vacuum. The fraction boiling at 76°–78° C./13 Pa is collected in a receiver flask, yielding 13.8 g of 4-formyl-2-methyl-2,4,4-trichlorobutyronitrile in the form of a colourless oil.

IR-spectrum (liquid) in cm$^{-1}$: 2250 (CN), 1750 (CO).
$^1$H-NMR-spectrum (60 MHz in CDCl$_3$) in ppm: 9.30 (s, 1H, —CHO); 3.22 (s, 2H, H$_2$ on C-3); 2.60 (s, 3H, —CH$_3$).

Elemental analysis for C$_6$H$_6$Cl$_3$NO (mol.wt. 214.48): calculated C 33.60%, H 2.82%, N 6.53%, Cl 49.59%; found C 34.1%, H 3.1%, N 6.8%, Cl 48.6%.

(b) Preparation of 2,5-dichloro-3-methylpyridine 21.4 g of the 4-formyl-2-methyl-2,4,4-trichlorobutyronitrile obtained in (a) are heated for 4 to 5 hours to 145° C. while introducing a weak stream of dry HCl gas. After it has cooled, the dark melt is subjected to steam distillation, affording 9.9 g of 2,5-dichloro-3-methylpyridine in the form of colourless crystals (recrystallised from $CH_3OH/H_2O$ in the volume ratio of 4:1).

$^1$H-NMR spectrum (60 MHz in $CDCl_3$) in ppm: 8.15 (d, 1H, H an C-6); 7.50 (d, 1H, H on C-4); 2.40 (s, 3H, —$CH_3$).

Elemental analysis for $C_6H_5Cl_2N$ (mol.wt. 162.02): calculated C 44.48%, H 3.11%, N 8.65%, Cl 43.77%; found C 44.4%, H 2.9%, N 7.9%, Cl 53.8%.

EXAMPLE 2

Single-step preparation of 2,5-dichloro-3-methylpyridine 14.7 g of trichloroacetaldehyde, 13.5 g of methacrylonitrile, 0.5 g of copper(I) chloride and 40 ml of acetonitrile are heated in a tantalum autoclave for 2 hours to 150° C. and then for a further 2 hours to 180° C. The solvent is then distilled off, the residue is taken up in 50 ml of diethyl ether, and the ethereal solution is filtered. The diethyl ether is distilled off in a water jet vacuum and the residue is subjected to steam distillation. The crystalline product is identical with the compound of Example 1(b).

EXAMPLE 3

(a) Preparation of 4-formyl-2,4-dichlorovaleronitrile 12.7 g of 2,2-dichloropropionaldehyde, 31.8 g of acrylonitrile, 0.3 g of copper powder and 30 ml of acetonitrile are heated in an enamel autoclave for 12 hours to 120° C. The solvent and excess acrylonitrile are distilled off in a water jet vacuum and the residue is taken up in 50 ml of diethyl ether. The ethereal solution is filtered and evaporated to dryness, and the residue is rectified in a high vacuum, affording 11.7 g of 4-formyl-2,4-dichlorovaleronitrile in the form of an oil which boils at 70°–74° C./13 Pa.

IR spectrum (liquid) in $cm^{-1}$: 2250 (CN), 1750 (CO).

$^1$H-NMR spectrum (100 MHz in $CDCl_3$) in ppm: 9.5 (s, 1H, —CHO); 4.75 (t, 1H, H on C-2); 2.3–3.1 (m, 2H, on C-3); 1.78 (s, 3H, —$CH_3$). The $^1$H-NMR spectrum shows the presence of two stereoisomers in the ratio of about 1:1.

Elemental analysis for $C_6H_7Cl_2NO$ (mol.wt. 180.03): calculated C 40.03%, H 3.93%, N 7.78%, Cl 39.39%; found C 41.0%, H 4.0%, N 7.9%, Cl 38.5%.

(b) Preparation of 2,3-dichloro-5-methylpyridine 18 g of the 4-formyl-2,4-dichlorovaleronitrile obtained in Example 3(a) and 0.1 g of copper powder are heated in a tantalum autoclave for 5 hours to 150° C. after the introduction of 10 g of dry HCl gas under pressure. After they have cooled, the contents of the autoclave are subjected to steam distillation, affording 10.5 g of 2,3-dichloro-5-methylpyridine in the form of colourless crystals with a melting point of 46°–47° C. $^1$H-NMR spectrum (100 MHz in $CDCl_3$) in ppm: 8.13 (d, 1H, H on C-6); 7.59 (d, 1H, H on C-4); 2.34 (s, 3H, —$CH_3$).

Elemental analysis for $C_6H_5Cl_2N$ (mol.wt. 162.02): calculated C 44.48%, H 3.11%, N 8.65%, Cl 43.77%; found C 44.5%, H 3.2%, N 8.6%, Cl 43.5%.

EXAMPLE 4

Single-step preparation of 2,3-dichloro-5-methylpyridine 12.7 g of 2,2-dichloropropionaldehyde, 8 g of acrylonitrile, 0.5 g of copper(I) chloride and 40 ml of acetonitrile are heated in a tantalum autoclave for 2 hours to 180° C. After they have cooled, the contents of the autoclave are taken up in 50 ml of diethyl ether. The ethereal solution is filtered, and the filtrate is concentrated in vacuo. The residue is subjected to steam distillation. The crystalline product is identical with the substance obtained in Example 3(b).

EXAMPLE 5

Single-step preparation of 2,3-dichloro-5-trichloromethylpyridine 23 g of pentachloropropionaldehyde, 8 g of acrylonitrile, 0.5 g of copper(I) chloride and 40 ml of acetonitrile are heated in a tantalum autoclave for 3 hours to 170° C. After they have cooled, the contents of the autoclave are taken up in 50 ml of diethyl ether and the ethereal solution is filtered. The filtrate is evaporated to dryness in vacuo and the residue is rectified. 2,3-Dichloro-5-trichloromethylpyridine is collected in a receiver (yield: 17.49 g). Boiling point: 147°–149° C./1700 Pa.

IR spectrum (KBr) in $cm^{-1}$: 3050, 1590, 1555, 1430, 1380, 1180, 1049.

$^1$H-NMR spectrum (100 MHz in $CDCl_3$) in ppm: 8.85 (d, J=5 Hz), 8.25 (d. J=5 Hz).

Elemental analysis for $C_6H_2Cl_5N$ (mol.wt. 265.35): calculated C 27.15%, H 0.75%, N 5.27%, Cl 66.80%; found C 27.1%, H 0.9%, N 5.3%, Cl 66.4%.

EXAMPLE 6

Preparation of 2,5-dichloro-3-trifluoromethylpyridine

The procedure of Example 5 is repeated, replacing pentachloropropionaldehyde by 14.1 g of trichloroacetaldehyde and acrylonitrile by 12.1 g of α-trifluoromethylacrylonitrile (prepared by the method of Darrall et al., Soc. 1951, 2330), to give 2,5-dichloro-3-trifluoromethylpyridine; $n_D^{25} = 1.4825$.

EXAMPLE 7

(a) Preparation of 4-formyl-2-methyl-2,4-dichlorovaleronitrile 12.7 g of 2,2-dichloropropionaldehyde, 13.5 g of methacrylonitrile, 0.5 of copper(I) chloride and 40 ml of acetonitrile are heated in a tantalum autoclave for 1 hour to 130° C. and then for 2 hours to 150° C. The solvent and excess methacrylonitrile are distilled off in a water jet vacuum and the residue is taken up in 50 ml of diethyl ether and the ethereal solution is filtered. The diethyl ether is distilled off in vacuo and the residue is rectified in a high vacuum. The fraction boiling at 76°–77° C./13 Pa is collected in a receiver. Yield: 10.8 g of 4-formyl-2-methyl-2,4-dichlorovaleronitrile in the form of a light brown oil.

IR spectrum (liquid) in $cm^{-1}$: 2250(CN), 1750(CO).

$^1$H-NMR spectrum (60 MHz in $CDCl_3$) in ppm: (mixture of diastereoisomers in the ratio 1:1) 9.71 and 9.53 respectively (s, 1H, —CHO); 2.96 (s, 4H, 2x-$CH_2$); 2.14

(s, 6H, 2x—CH₃); 2.02 (s.3H, —CH₃) 1.93 (s, 3H, —CH₃).

Elemental analysis for C₇H₉Cl₂NO (mol.wt. 194.06): calculated: C 43.22%, H 4.67%, N 7.21%, Cl 36.53%; found: C 43.6%, H 4.6%, N 7.3%, Cl 35.9%.

(b) Preparation of 2-chloro-3,5-dimethylpyridine 19.4 g of the 4-formyl-2-methyl-2,4-dichlorovaleronitrile obtained in Example 7(a) are heated for 4 hours to 160°–170° C. while introducing a weak stream of dry HCl gas. After it has cooled, the dark melt is subjected to steam distillation. The distillate is extracted with diethyl ether and the extract is dried and evaporated to dryness in vacuo. The residual light brown oil is distilled, affording 7.36 g of 2-chloro-3,5-dimethylpyridine in the form of a light brown oil which boils at 110° C./2500 Pa.

¹H-NMR spectrum (60 MHz in CDCl₃) in ppm: 8.0 (d, 1H, H on C-6); 7.31 (d, 1H, H on C-4, J₆₋₄=2.0 Hz); 2.34 (s, 3H, —CH₃); 2.28 (s, 3H, —CH₃).

Elemental analysis for C₇H₈ClN (mol.wt. 141.60): calculated: C 59.38%, H 5.65%, N 9.83%, Cl 25.04%; found C 59.1%, H 5.9%, N 9.7%, Cl 25.3%.

The ¹H-NMR spectral data show that the compound is identical with the 2-chloro-3,5-lutidine described in J.Chem. Soc. Perkin I (1979), 1578.

EXAMPLE 8

Single-step process for the preparation of 2-chloro-3,5-dimethylpyridine

The procedure of Example 4 is repeated, using 10 g of methacrylonitrile instead of acrylonitrile, to give the 2-chloro-3,5-dimethylpyridine described in Example 7(b).

EXAMPLE 9

(a) Preparation of 2,2-dichloro-3,3,3-trifluoropropionaldehyde 19.2 g of ozone (admixed with oxygen) are introduced at 20° C. into a solution of 100.4 g of 4,4-dichloro-5,5,5-trifluoro-2-methyl-2-pentenecarboxylic acid methyl ester in 800 ml of glacial acetic acid. Then a suspension of 15 g of zinc dust in 15 ml of water is added and 2,2-dichloro-3,3,3-trifluoropropionaldehyde is distilled off under normal pressure. Yield: 52.8 g of product in the form of a colourless liquid with a pungent odour. Boiling point: 66°–67° C.

IR (CCl₄): $\nu_{CO}$ 1770 cm⁻¹
¹H-NMR (CDCl₃): δ=9.3 (q, J=2 Hz) ppm.
Analysis: C₃HCl₂F₃O (180.9); calculated: C 19.92%, H 0.56%, F 31.50%, Cl 39.19%; found: C 20.2%, H 0.8%, F 30.9%, Cl 38.5%.

(b) Preparation of 4-formyl-2,4-dichloro-5,5,5-trifluorovaleronitrile

A mixture of 36 g of 2,2-dichloro-3,3,3-trifluoropropionaldehyde, 80 ml of acetonitrile, 80 ml of acrylonitrile and 0.5 g of copper (I) chloride is heated in a tantalum autoclave for 12 hours to 120° C. After working up as described in Example 1(a), 4-formyl-2,4-dichloro-5,5,5-trifluorovaleronitrile is obtained as a colourless oil; boiling point: 85°–86° C./900 Pa.

IR (CCl₄): $\nu_{CN}$ 2550 cm⁻¹, $\nu_{CO}$ 1750 cm⁻¹.
¹H-NMR (CDCl₃): δ=9.56 (m, 1H, CHO); 4.7 (m, 1H, C-2-3); 2.7–3.3 (m, 2H, C-3-H) ppm (mixture of diastereoisomers).
Analysis: C₆H₄Cl₂F₃NO (234.0): calculated: C 30.80%, H 1.73%, N 5.99%, F 24.36%; found: C 31.5%, H 2.0%, N 5.9%, F 23.8%.

(c) Preparation of 2,3-dichloro-5-trifluoromethylpyridine 25 g of the 4-formyl-2,4-dichloro-5,5,5-trifluorovaleronitrile obtained in Example 9(b) and 0.1 g of copper powder are heated in a tantalum autoclave for 5 hours to 170° C. Steam distillation of the contents of the autoclave yields 11.9 g of 2,3-dichloro-5-trifluoromethylpyridine as a colourless oil with a peppermint odour.

Boiling point: 80° C./3325 Pa. ¹H-NMR (CDCl₃): δ=8.63 (d, J=2 Hz, 1H); 8.03 (d, J=2 Hz, 1H) ppm.
Analysis: C₆H₂Cl₂F₃N (216.0): calculated: C 33.36%, H 0.93%, N 6.48%, Cl 32.82%, F 26.38%; found: C 33.5%, H 1.0%, N 6.5%, Cl 33.4%, F 25.9%.

EXAMPLE 10

Single-step process for the preparation of 2,3-dichloro-5-trifluoromethylpyridine The batch employed in Example 9(b) is heated in accordance with the particulars of Example 2, affording 2,3-dichloro-5-trifluoromethylpyridine, which is identical with the product obtained in Example 9(c).

What is claimed is:
1. 2,2-Dichloro-3,3,3-trifluoropropionaldehyde.

* * * * *